US00PP20285P2

(12) United States Plant Patent
Takamura

(10) Patent No.: US PP20,285 P2
(45) Date of Patent: Sep. 8, 2009

(54) ***VIOLA* PLANT NAMED 'SUNVIOPAPUHO'**

(50) Latin Name: Sunviopapuho
Varietal Denomination: *Viola cornuta*

(75) Inventor: Naoto Takamura, Yamanashi (JP)

(73) Assignee: Suntory Flowers Limited, Tokyo (JP)

( * ) Notice: Subject to any disclaimer, the term of this patent is extended or adjusted under 35 U.S.C. 154(b) by 126 days.

(21) Appl. No.: 11/903,543

(22) Filed: Sep. 21, 2007

(51) Int. Cl.
*A01H 5/00* (2006.01)

(52) U.S. Cl. ..... Plt./323
(58) Field of Classification Search ..... Plt./323, Plt./263.1
See application file for complete search history.

*Primary Examiner*—Howard J Locker
(74) *Attorney, Agent, or Firm*—C. A. Whealy

(57) ABSTRACT

A new and distinct cultivar of *Viola* plant named 'Sunviopapuho', characterized by its compact and mounding plant habit; freely branching habit; freely flowering habit; and purple and white bi-colored flowers.

1 Drawing Sheet

Botanical designation: *Viola cornuta.*
Cultivar denomination: 'Sunviopapuho'.

BACKGROUND OF THE INVENTION

The present invention relates to a new and distinct cultivar of *Viola,* botanically known as *Viola cornuta* and hereinafter referred to by the name 'Sunviopapuho'.

The new *Viola* is a product of a planned breeding program conducted by the Inventor in Higashiomi, Shiga, Japan. The objective of the breeding program was to create new compact *Viola* cultivars with attractive flower coloration.

The new *Viola* originated from a cross-pollination made by the Inventor in April, 2003, in Higashiomi, Shiga, Japan, of a proprietary selection of *Viola cornuta* identified as code number 0V-41-1, not patented, as the female, or seed, parent with a proprietary selection of *Viola cornuta* identified as code number 01V-135-3, not patented, as the male, or pollen, parent. The new *Viola* was discovered and selected by the Inventor as a single flowering plant within the progeny of the stated cross-pollination in a controlled environment in Higashiomi, Shiga, Japan.

Asexual reproduction of the new *Viola* by vegetative cuttings in a controlled environment in Higashiomi, Shiga, Japan since April, 2005, has shown that the unique features of this new *Viola* are stable and reproduced true to type in successive generations.

SUMMARY OF THE INVENTION

The cultivar Sunviopapuho has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunviopapuho'. These characteristics in combination distinguish 'Sunviopapuho' as a new and distinct cultivar of *Viola:*

1. Compact and mounding plant habit.
2. Freely branching habit.
3. Freely flowering habit.
4. Purple and white bi-colored flowers.

Compared to plants of the female parent selection, plants of the new *Viola* are smaller and have larger flowers. In addition, plants of the new *Viola* and the female parent selection differ in flower color as plants of the female parent selection have white-colored flowers. Compared to plants of the male parent selection, plants of the new *Viola* differ primarily in flower color as plants of the male parent selection have blue and white bi-colored flowers.

Plants of the new *Viola* can also be compared to plants of the cultivar Sunviobuho, disclosed in U.S. Plant Pat. No. 16,557. In side-by-side comparisons conducted in Higashiomi, Shiga, Japan, plants of the new *Viola* and the cultivar Sunviobuho differed in the following characteristics:

1. Plants of the new *Viola* were smaller than plants of the cultivar *Sunviobuho*.
2. Plants of the new *Viola* had shorter lateral branches and peduncles than plants of the cultivar Sunviobuho.
3. Plants of the new *Viola* had shorter leaves than plants of the cultivar *Sunviobuho*.
4. Plants of the new *Viola* had larger flowers than plants of the cultivar Sunviobuho.
5. Plants of the new *Viola* and the cultivar Sunviobuho differed in flower color.

BRIEF DESCRIPTION OF THE PHOTOGRAPHS

The accompanying colored photographs illustrate the overall appearance of the new *Viola,* showing the colors as true as it is reasonably possible to obtain in colored reproductions of this type. Colors in the photographs may differ slightly from the color values cited in the detailed botanical description which accurately describe the colors of the new *Viola.*

The photograph at the top of the sheet comprises a side perspective view of a typical flowering plant of 'Sunviopapuho' grown in a container.

The photograph at the bottom of the sheet is a close-up view of typical flowers of 'Sunviopapuho'.

DETAILED BOTANICAL DESCRIPTION

The aforementioned photographs and following observations, measurements and values describe plants grown in Higashiomi, Shiga, Japan, under commercial practice during the winter in a polyethylene-covered greenhouse with day temperatures ranged from 10° C. to 23° C. and night temperatures ranging from −2° C. to 6° C. Plants had been growing for about five months when the photographs and description were taken. In the following description, color references are made to The Royal Horticultural Society Colour Chart, 2001 Edition, except where general terms of ordinary dictionary significance are used.

Botanical classification: *Viola cornuta* cultivar Sunviopapuho.

Parentage:

*Female, or seed, parent.*—Proprietary selection of *Viola cornuta* identified as code number 0V-41-1, not patented.

*Male, or pollen, parent.*—Proprietary selection of *Viola cornuta* identified as code number 01V-135-3, not patented.

Propagation:

*Type.*—By vegetative cuttings.

*Time to initiate roots.*—About two weeks at 20° C. to 25° C.

*Time to produce a rooted young plant roots.*—About four weeks at 20° C. to 25° C.

*Root description.*—Fine, fibrous and fleshy; light brown in color.

*Rooting habit.*—Freely branching.

Plant description:

*Plant form/habit.*—Compact and mounded plant habit; outwardly spreading; vigorous growth habit. Freely branching habit; pinching enhances branching.

*Plant height.*—About 17 cm.

*Plant width (spread).*—About 29.4 cm.

*Lateral branches.*—Length: About 8.8 cm. Diameter: About 1.9 mm. Internode length: About 1.6 cm. Strength: Strong. Texture: Smooth, glabrous. Color: 146D.

Foliage description:

*Arrangement.*—Alternate, simple.

*Length.*—About 2.1 cm.

*Width.*—About 1.4 cm.

*Shape.*—Elliptic.

*Apex.*—Obtuse to rounded.

*Base.*—Truncate.

*Margin.*—Crenate.

*Texture, upper and lower surfaces.*—Smooth, glabrous.

*Venation pattern.*—Pinnate; reticulate.

*Color.*—Developing and fully expanded leaves, upper surface: 137B; venation, N144D. Developing and fully expanded leaves, lower surface: 147B; venation, N144D.

*Petiole.*—Length: About 1.8 cm. Diameter: About 0.8 mm. Texture, upper and lower surfaces: Smooth, glabrous. Color, upper and lower surfaces: 144B.

*Stipule.*—Length: About 1.8 cm. Diameter: About 1.1 cm. Shape: Pinnately-parted. Apex: Obtuse to rounded. Base: Obtuse. Texture, upper and lower surfaces: Smooth, glabrous. Color, upper surface: 137B. Color, lower surface: 147B.

Flower description:

*Flower type/habit.*—Single flowers borne in upper leaf axils; flowers face obliquely upright. Freely flowering habit with about 57 open flowers per plant.

*Fragrance.*—None detected.

*Natural flowering season.*—Continuously flowering from early November to June in Japan. Flowers not persistent.

*Postproduction longevity.*—Flowers last about five to seven days on the plant.

*Flower buds.*—Height: About 1.4 cm. Diameter: About 4 mm. Shape: Lenticular. Color: N81A.

*Flower diameter.*—About 3.6 cm by 3.1 cm.

*Flower depth.*—About 1.5 cm.

*Eye diameter.*—About 1.8 mm by 2.5 mm.

*Petals.*—Quantity per flower: Typically five in a single whorl; one upper petal, two lateral petals and lower two petals fused and spurred. Upper petal: Length: About 1.9 cm. Diameter: About 1.9 cm. Shape: Spatulate with rounded apex and attenuate base; margin, entire and slightly undulate. Texture, upper and lower surfaces: Smooth, glabrous. Color: Developing and fully expanded petals, upper surface: N81A, color becoming closer to N82C with development. Developing and fully expanded petals, lower surface: N81A, color becoming closer to N82C with development. Lateral petals: Length: About 1.5 cm. Diameter: About 1.6 cm. Shape: Spatulate with rounded apex and attenuate base; margin, entire and slightly undulate. Texture, upper and lower surfaces: Smooth, glabrous. Color: Developing and fully expanded petals, upper surface: 155B; occasionally tinted with close to N81A; venation, N92C. Developing and fully expanded petals, lower surface: N155B. Lower fused petals: Length: About 1.5 cm. Diameter: About 2.2 cm. Shape: Reniform with cordate apex and attenuate base; margin, entire and slightly undulate. Texture, upper and lower surfaces: Smooth, glabrous. Color: Developing and fully expanded petals, upper surface: 155B; occasionally tinted with close to N81A; venation, N92C; eye, 21B. Developing and fully expanded petals, lower surface: N155B. Spur length: About 6.1 mm. Spur diameter: About 1.3 mm. Spur color: 90A.

*Sepals.*—Quantity per flower: Typically five in a single whorl. Length: About 1.2 cm. Width: About 3.1 mm. Shape: Lanceolate. Apex: Acute. Base: Truncate. Margin: Entire. Texture, upper and lower surfaces: Smooth, glabrous. Color, upper and lower surfaces: 144A.

*Peduncles.*—Length: About 10.4 cm. Diameter: About 1.3 mm. Texture: Smooth, glabrous. Color: 144B.

*Reproductive organs.*—Stamens: Quantity per flower: Typically five. Anther shape: Ellipsoidal. Anther size: About 2.8 mm by 1 mm. Anther color: 10D. Pollen amount: Scarce. Pollen color: Close to 10D. Pistils: Quantity per flower: One. Pistil length: About 4 mm. Stigma shape: Ellipsoidal. Stigma color: 153D. Style color: Close to 155D. Ovary color: 144B.

*Seed/fruit.*—Seed and fruit development have not been observed.

Disease/pest resistance: Plants of the new *Viola* have not been noted to be resistant to pathogens and pests common to *Viola*.

Garden performance: Plants of the new *Viola* have been observed to have good garden performance and tolerate rain, wind and temperatures from about −7° C. to about 25° C.

It is claimed:

1. A new and distinct *Viola* plant named 'Sunviopapuho' as illustrated and described.

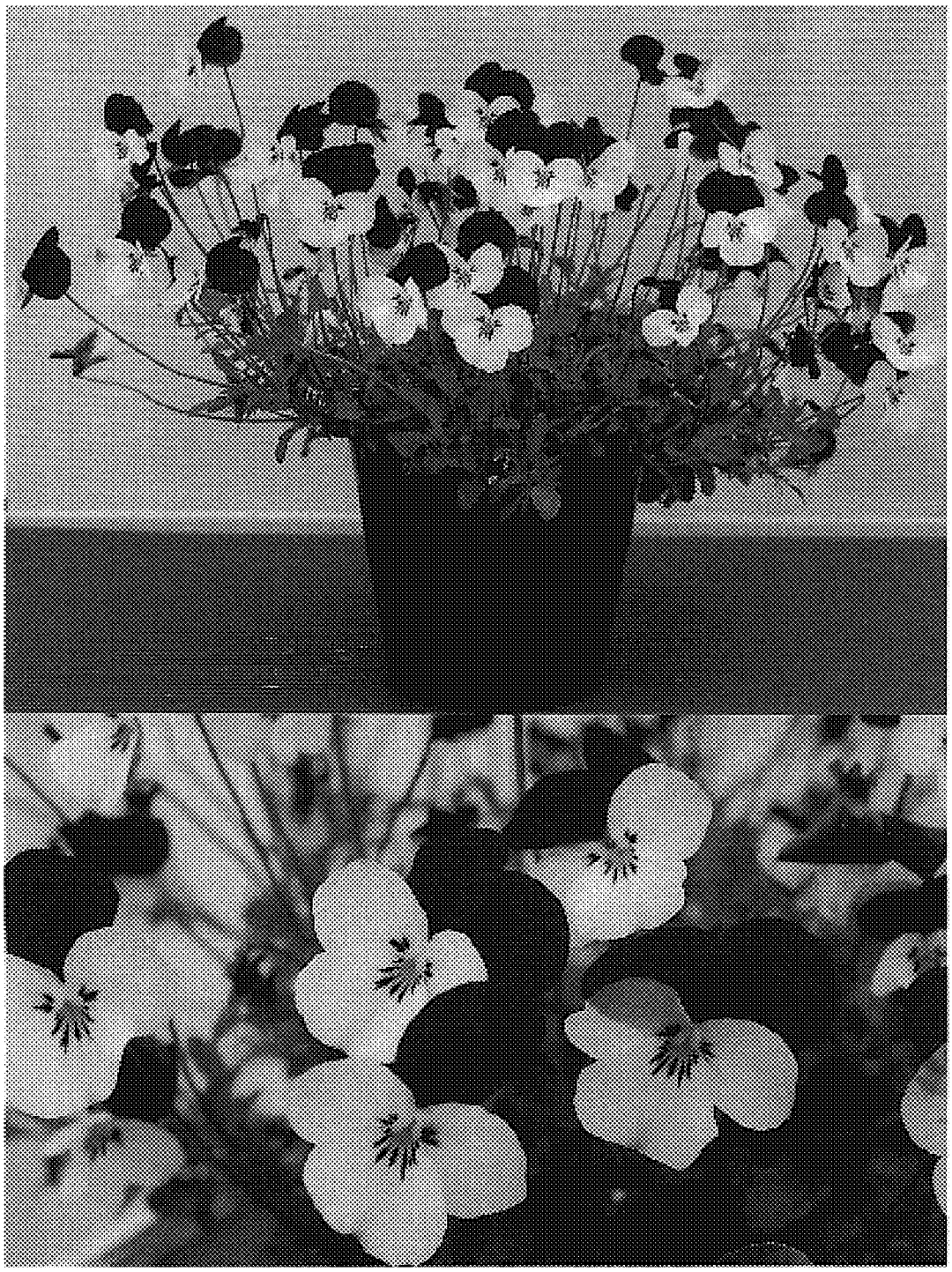

* * * * *